United States Patent [19]
Shahid et al.

[11] Patent Number: 5,967,775
[45] Date of Patent: Oct. 19, 1999

[54] DENTAL COLOR COMPARATOR DEVICE

[75] Inventors: Ehab Shahid, Valley cottage, N.Y.; Nicholas J. Webb, Wrightwood, Calif.

[73] Assignee: Dental Devices, LLC, San Antonio, Tex.

[21] Appl. No.: 08/887,475

[22] Filed: Jul. 2, 1997

[51] Int. Cl.[6] .............................. A61C 1/00; A61C 3/00; A61C 19/10
[52] U.S. Cl. ................................. 433/29; 433/26
[58] Field of Search ............... 433/26, 29, 215, 433/229

[56] References Cited

U.S. PATENT DOCUMENTS

| | | | |
|---|---|---|---|
| 1,449,165 | 3/1923 | Cameron | 362/120 |
| 2,449,435 | 9/1948 | Whittemore | 433/26 |
| 2,502,014 | 3/1950 | Loggie | 88/14 |
| 3,436,157 | 4/1969 | Adler et al. | 356/192 |
| 3,773,425 | 11/1973 | Bentley | 356/42 |
| 3,986,777 | 10/1976 | Roll | 356/176 |
| 4,291,985 | 9/1981 | Tsujimura | 356/408 |
| 4,523,852 | 6/1985 | Bauer | 356/421 |
| 4,527,895 | 7/1985 | Rubin | 356/30 |
| 4,534,644 | 8/1985 | Beesley | 356/30 |
| 4,608,015 | 8/1986 | Smigel | 433/26 |
| 4,654,794 | 3/1987 | O'Brien | 364/413 |
| 4,836,674 | 6/1989 | Lequime et al. | 356/319 |
| 4,885,667 | 12/1989 | Selden | 362/253 |
| 4,978,296 | 12/1990 | Antons et al. | 433/26 |
| 5,064,281 | 11/1991 | Davis | 356/30 |
| 5,351,424 | 10/1994 | Schulle | 38/102.1 |
| 5,383,020 | 1/1995 | Vieillefosse | 356/326 |
| 5,398,216 | 3/1995 | Ahuja | 362/253 |
| 5,428,450 | 6/1995 | Vieillefosse et al. | 356/405 |
| 5,636,984 | 6/1997 | Gomes | 433/30 |

OTHER PUBLICATIONS

Article by Bergen et al. entitled "Dental Operatory Lighting and Tooth Color Discrimination", JADA, vol. 94, Jan. 1977, pp. 130–134.
Article by Sproull entitled "Color Matching in Dentistry: The Three–Dimensional Nature of Color", Journal of Prosthetic Dentistry, vol. 29, No. 4, Apr. 1973, pp. 416–422.
Advertisement for Esthelite Shade Matching Light, at least as early as May 16, 1997.

Primary Examiner—Nicholas D. Lucchesi
Attorney, Agent, or Firm—David P. Gordon; David S. Jacobson; Thomas A. Gallagher

[57] ABSTRACT

A dental comparator device includes a body, a polychromatic light emitter within the body, and a magnifying lens and holder for a dental standard coupled to the body. The standard holder is either a clip, a hub for receiving a plurality of radially aligned standards, or a magnetic standard holder. According to one embodiment, the body is elongate and the light source and magnifying lens are provided at one end of the elongate body. The light source is a halogen bulb powered by batteries. The magnifying lens is oriented perpendicular to the body. Coupled to the lens is a light-transmitting ring-shaped member for directing light to one side of the lens, to thereby illuminate a tooth and standard situated before the transparent tubular-shaped member. According to another embodiment, two booms are coupled to the body. One boom is provided with a standard holder at its distal end and the other boom is provided with a magnifying lens at its distal end. The booms are preferably articulable, and the standard holder and magnifying lens are preferably adjustable in orientation. According to yet another embodiment, the body includes two booms, one for a standard holder and the other for a magnifying lens. Polychromatic light is transmitted by a fiber optic cable extending from a light source to a distal end of the body.

19 Claims, 4 Drawing Sheets

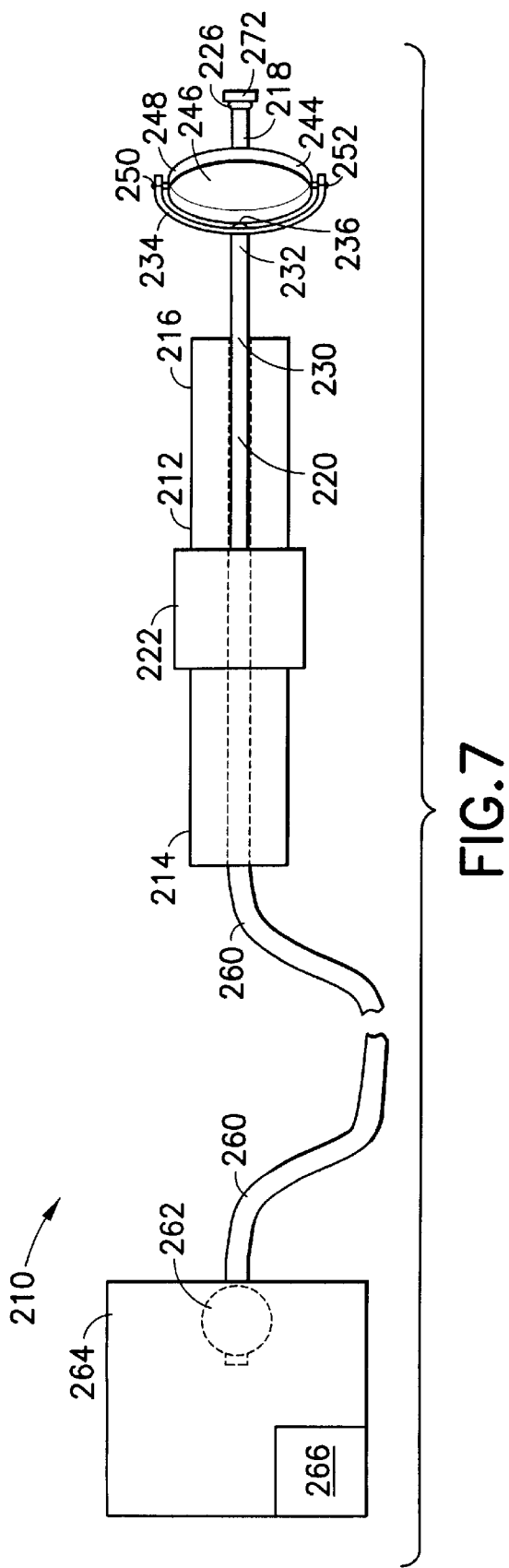
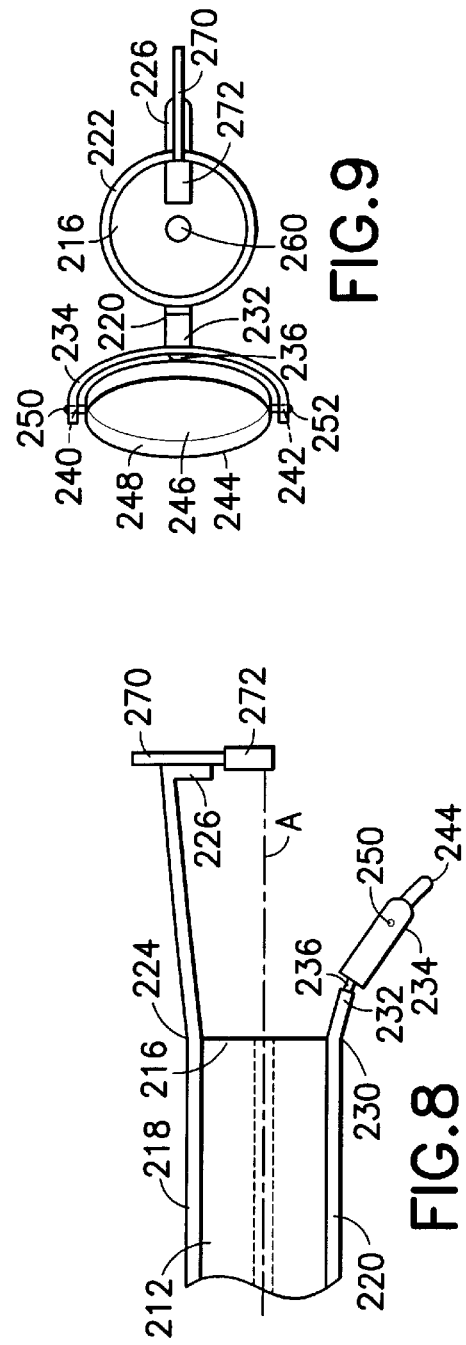

DENTAL COLOR COMPARATOR DEVICE

BACKGROUND OF THE INVENTION

1. Field of the Invention

This invention relates broadly to dental devices. More particularly, this invention relates to a device for accurately matching colored dental standards to natural teeth.

2. State of the Art

Prior to the process of implanting a dental prosthesis (or prosthetic tooth) in the mouth of a dental patient, a dentist must make a decision as to the color to be used for the dental prosthesis such that dental prosthesis appears natural when implanted adjacent natural teeth. To assist the dentist in making a decision, dental standards are available to permit the dentist to compare the standards against the natural teeth. The standards are typically preformed dental prostheses of a variety of colors, saturations, or hues, attached to the end of a thin metal rod. Once the dentist decides which standard is closest in color to the natural teeth, the appropriate color for the prosthetic is thereby chosen.

However, choosing the correct color standard relative to natural teeth is often difficult. One difficulty lies in that natural teeth are translucent and, as a result, the type of light in which they are viewed can affect their apparent color. For example, tooth color appears to change when viewed in fluorescent light and then polychromatic light (or white light) such as daylight. However, dental offices are typically lit with fluorescent lighting. Some dentists have used standard incandescent bulbs to provide a wider spectrum of light when comparing standards to the natural teeth. However, standard incandescent bulbs do not provide the broad polychromatic spectrum of light necessary to properly evaluate the standards relative to the natural teeth. Tooth color also appears to change when viewed in direct light and shadow. Furthermore, the background against which natural teeth and standards are viewed can alter the color appearance of the standards relative to the natural teeth. Moreover, natural teeth are multicolored, and the process of selecting the color for the prothesis requires a careful assessment of the topography and predominant color of the natural teeth, especially the teeth which will be adjacent the implanted prosthesis.

Therefore, a number of devices have been proposed to assist a dentist in choosing the color for a dental prosthesis tooth. U.S. Pat. No. 3,436,157 to Adler discloses a prismatic comparator device using a polychromatic light source which enables natural teeth to be simultaneously viewed with standards for comparison. The device however is cumbersome comprising four relatively long tubes, of which the ends of two must be inserted in the patient's mouth to abut the patient's natural teeth. In addition, the light source is a projection bulb, requiring a large amount of power (i.e., an AC power source) for illumination and generating a large amount of heat.

Other devices attempt to remove dentist subjectivity and determine the appropriate color for a prosthetic tooth based on an objective determination of the appropriate tooth color. For example, U.S. Pat. No. 5,383,020 to Vieillefosse discloses a device which uses a spectrometer to measure the reflectance of a natural tooth surface, amplifies the reflectance signal, converts the amplified reflectance signal to a digital signal, and processes the digital signal to provide an output purportedly helpful in determining prosthetic tooth color. U.S. Pat. No. 5,428,450 to Vieillefosse et al. discloses another electronic device. The device illuminates a portion of the natural tooth with a uniform and isotropic diffuse "light flux" and receives the light backscattered from the tooth. The backscattered light is then spectrally analyzed to purportedly determine the appropriate color for a prosthetic tooth. U.S. Pat. Nos. 3,986,777 to Roll, 4,654,794 to O'Brien, and U.S. Pat. No. 4,836,674 to Lequime et al. disclose other electronic spectrometric devices. However, these device are complicated and costly to manufacture. In addition, these devices do not account for the fact that teeth are multicolored. Aiming the device at one portion of natural tooth may provide results which differ when the device is aimed at another portion of the tooth, such that a subdominant color value, rather than the predominant color value, is used for selecting the color for the dental prosthesis. Moreover, the human eye, which will eventually judge the finished product, is removed from the comparison process.

SUMMARY OF THE INVENTION

It is therefore an object of the invention to provide a dental comparator device which can be used to appropriately select the color of a dental prosthesis.

It is also an object of the invention to provide a dental comparator device which can be used to simultaneously magnify a natural tooth and a prosthetic tooth color standard.

It is a further object of the invention to provide a dental comparator device which does not eliminate the subjectivity of the dentist in choosing a color for a dental prosthesis.

It is another object of the invention to provide a dental comparator device which is relatively small in size, easy to manipulate, and portable.

It is an additional object of the invention to provide a dental comparator which is inexpensive, easy to manufacture, and uses relatively low power.

In accord with these objects, which will be discussed in detail below, a dental comparator device is provided having a body, a polychromatic light emitter within the body, and a magnifying lens and holder for a dental standard coupled to the body. Preferably, the polychromatic light source is a relatively small low voltage halogen bulb, providing a broad spectrum of white light, although other broad spectrum light sources may be used.

According to one embodiment of the invention, the body of the dental comparator device is elongate and the light source and magnifying lens are provided at one end of the elongate body. The light source is powered by batteries provided in the body. The magnifying lens is oriented perpendicular to the body. Coupled to the lens is a light-transmitting ring-shaped member for directing light to one side of the lens, to thereby polychromatically illuminate a tooth and standard situated before the transparent tubular-shaped member. The standard holder is either an adjustable clip, a rotatable hub adapted to receive a plurality of radially aligned standards, or a magnetic standard holder.

According to another embodiment of the invention, the body of the dental comparator device is elongate and the light source is provided at one end of the elongate body. Two booms are coupled to the body. One boom is provided with a standard holder at its distal end and the other boom is provided with a magnifying lens at its distal end. The booms are preferably articulable, and the standard holder and magnifying lens are preferably adjustable in orientation.

According to yet another embodiment of the invention, the dental comparator device body includes two booms, one for a standard holder and the other for a magnifying lens. Polychromatic light is transmitted by a fiber optic cable extending from a light source to a distal end of the body.

In operation, a standard is coupled to the standard holder such as by clamping an individual standard in a alligator clip, magnetically coupling the metal post of an individual standard to a magnetic holder, or by providing a standard wheel to a post for receiving the wheel. The dental comparator device is powered to provide polychromatic light, and the light is directed at the natural teeth of the patient and at the dental standard. The dentist orients the magnifying lens such that he or she may simultaneously view through the magnifying lens for comparison a natural tooth and a dental standard, both illuminated by polychromatic light. If the visual comparison shows that the colors of the natural tooth or teeth and the dental standard are not the same, the dental standard is then changed until a standard having a matching color is selected.

With the provided embodiments, the dental comparator device is small, lightweight, and easy to manipulate. Providing the dental standard in a holder permits a comparison to be easily made between the natural tooth and the standard. It will be appreciated that the dental comparator device permits a dentist to subjectively contribute to the color selection process for a prosthetic tooth.

Additional objects and advantages of the invention will become apparent to those skilled in the art upon reference to the detailed description taken in conjunction with the provided figures.

BRIEF DESCRIPTION OF THE DRAWINGS

FIG. 7 is a broken side elevation of a third embodiment of a dental comparator device;

FIG. 8 is a broken top view of the distal end of the dental comparator device of FIG. 7; and FIG. 9 is a distal end view of the dental comparator device of FIG. 7.

DETAILED DESCRIPTION OF THE PREFERRED EMBODIMENTS

Figure 1:
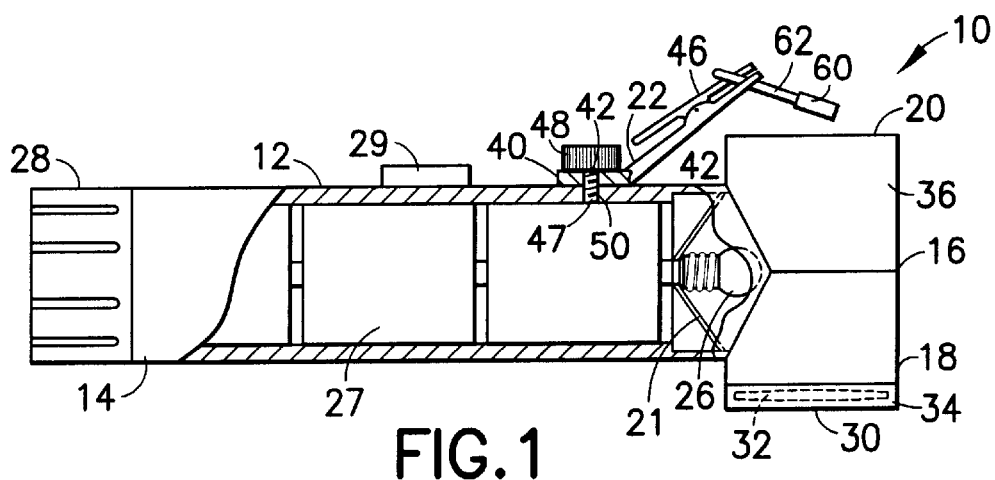
FIG. 1 is a partial cutaway side elevation of a first embodiment of dental comparator device of the invention.
Figure 2:
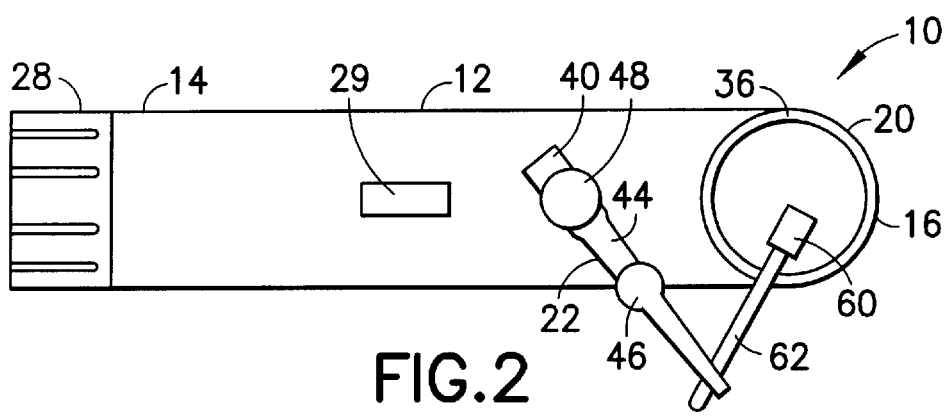
FIG. 2 is a top view of the dental comparator device of FIG. 1.
Figure 3:
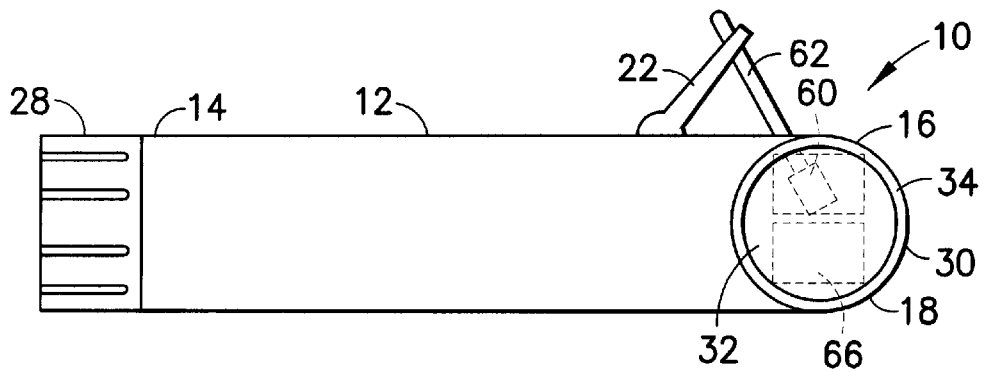
FIG. 3 is a bottom view of the dental comparator device of FIG. 1.

Turning now to FIGS. 1 through 3, a dental comparator device 10 according to a first embodiment of the invention is shown. The dental comparator device generally includes an elongate tubular body 12 having a first end 14 generally co-axial with the remainder of the body and a second end 16 generally perpendicular to the remainder of the body. The second end 16 includes a first viewing side 18 and a second illuminating side 20 opposite the viewing side, both of which will be further described below. A boom 22 is coupled to the body 12, preferably in a rotatable fashion. A polychromatic light source 26 is provided within the body and is powered by a DC power source 27, e.g., three 1.5 volt batteries, which is inserted into the body by removing an end cap 28 thread onto the first end 14. A power switch 29 is provided to supply and remove power from the power source 27 to the polychromatic light source 26. Preferably, the polychromatic light source 26 is a relatively low voltage halogen bulb, providing a broad spectrum of white light which is held in place by a holder or reflector 21.

The viewing side 18 of the second end 16 of the body 12 is coupled to a magnifying lens eyepiece or loupe 30. The magnifying lens eyepiece 30 is a magnifying lens 32 provided in a tubular holder 34. The tubular holder 34 is provided with threads (not shown) on one side for threadably coupling with the viewing side of the second end of the body. Preferably the magnifying lens 32 is powered to provide between two and twenty times magnification, and most preferably provides ten times magnification. It will be appreciated that because the tubular holder 34 is threaded, one threaded magnifying lens eyepiece 30 may be substituted with another threaded magnifying lens eyepiece having a lens of a different power. The illuminating side 20 of the second end 16 includes a transparent (or otherwise light transmitting) ring-shaped member 36. Polychromatic light (or white light) from the light source is directed to the illuminating side 20 through the ring-shaped member 36.

The boom 22 includes an attachment portion 40 having a bore 42 therethrough, and a distal portion 44 provided with a clip or clamp 46, e.g. an alligator clamp. The attachment portion 40 of the boom 22 is coupled to the body 12 using a set screw 47 having a large, preferably knurled head 48 which is easily engageable by the fingers of a dentist. The set screw 47 extends through the bore 42 and is thread into a threaded hole 50 in the body 12 to secure the boom 22 in a desired position.

A plurality of dental standards are provided for use with the dental comparator device. Each dental standard, e.g., dental standard 60, is preferably an injection-molded prosthetic tooth of a particular color, saturation, and hue, and is coupled to the end of a metal post 62.

In operation, a dental standard which appears to the naked eye to approximate the color of the natural teeth 66 of a patient is clamped in the clamp 46 at the post 62. If necessary, the boom 22 is adjusted, by loosing and re-tightening the set screw 47, to position the dental standard 60 over the illuminating side 20 of the second end 16 of the device 10. The power switch 29 is then moved to supply power to the polychromatic light source 26, and the illuminating side 20 and dental standard 60 are brought close to the mouth, and the natural teeth of the patient. Light is transmitted through the illuminating side and simultaneously illuminates the dental standard 60 and one or more of the natural teeth 66. The dentist views both the dental standard and at least a portion of one or more natural teeth through the magnifying lens 32 and is able to assess whether the color of the dental standard 60 is a match to the color of the natural tooth or teeth 66. Based on the subjective assessment, the dentist may judge the color of the dental standard to match the color of the natural teeth, or may alternatively substitute another dental standard in the standard holder 22, which the dentist believes will be a closer match. The process is repeated until a dentist is satisfied that a match between a dental standard and the natural teeth has been made. Once an appropriately colored dental standard is selected, the dentist uses the color properties of the dental standard to formulate a color for the prosthetic tooth (or teeth) of the patient.

Figure 4:
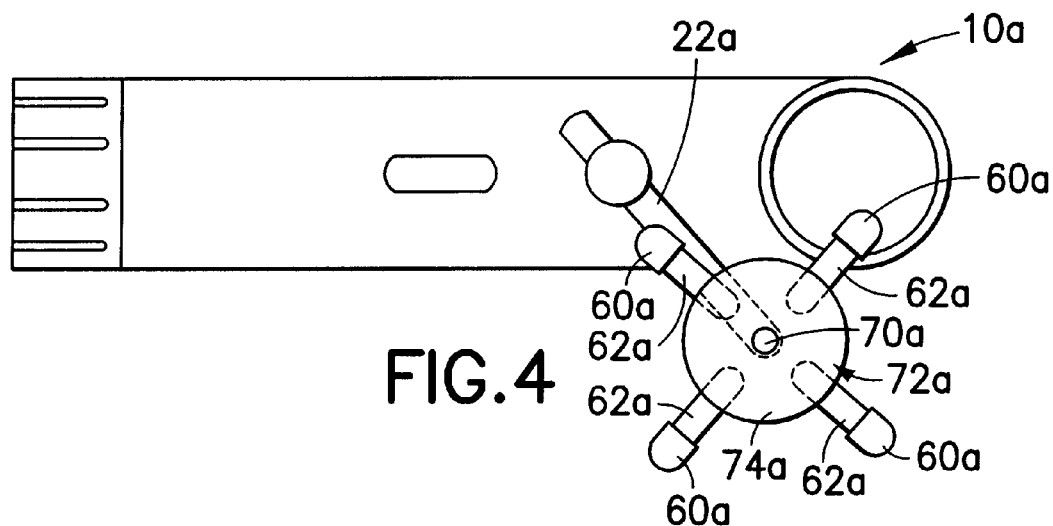
FIG. 4 is a top view of an alternate first embodiment of the dental comparator device including a modified standard holder.
Figure 4A:
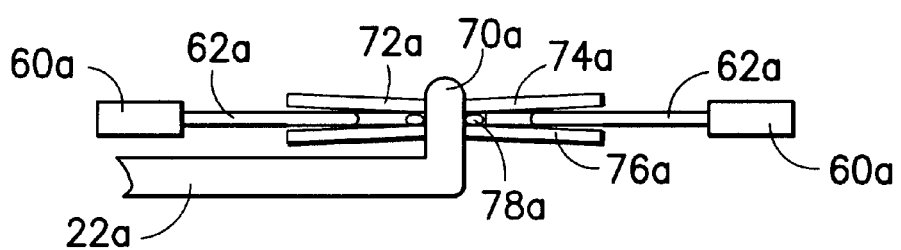
FIG. 4A is a broken partial side elevation view of the dental comparator device of FIG. 4.

Referring to FIGS. 4 and 4A, an alternate first embodiment of a dental comparator device is shown. The device 10a is the same as the device 10 described above, with the exception of the boom 22a. Instead of having a clamp for holding a dental standard, the boom 22a is provided with an axle 70a and a hub 72a rotatable about the axle. The hub 72a includes two preferably resilient discs 74a, 76a coupled at a central portion 78a. The discs 74a, 76a are adapted to frictionally receive therebetween the metal posts 62a of a plurality of radially aligned dental standards 60a. The dental standards preferably each have a different color or saturation or hue. A "standard wheel" is thereby formed which enables the dentist to compare several dental standards 60a with a patient's natural teeth by rotating the "standard wheel" about the axle 70a rather than by removing and substituting a new dental standard in a clamp.

Figure 5:
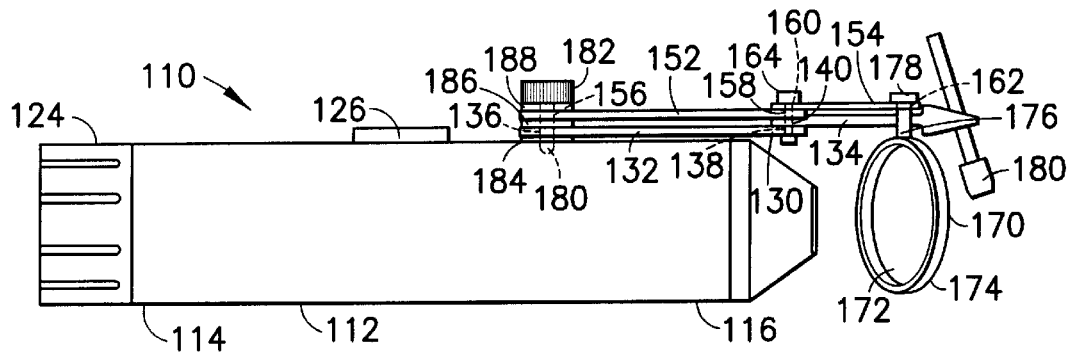
FIG. 5 is side elevation of a second embodiment of a dental comparator device of the invention.
Figure 6:
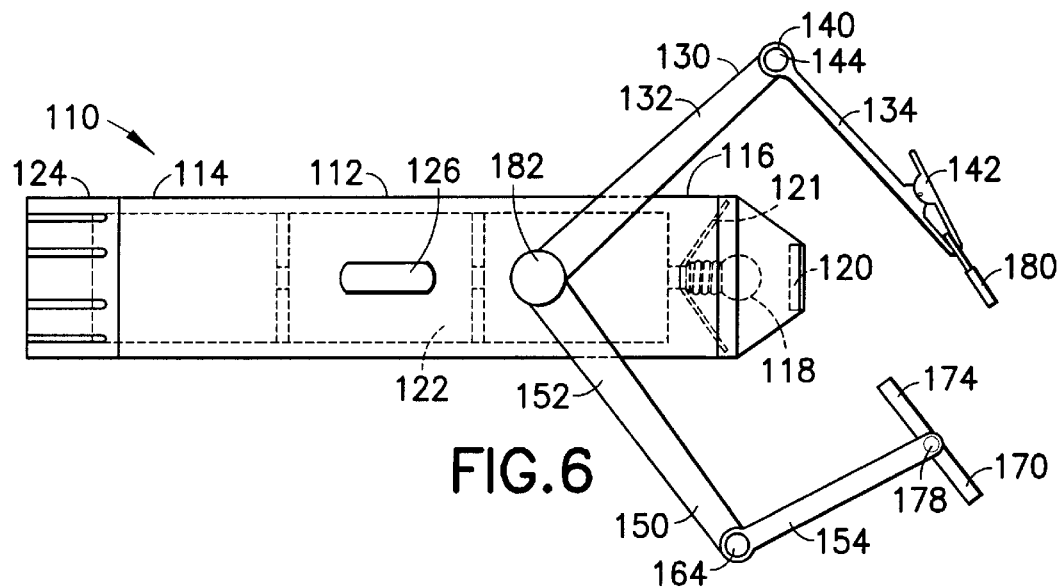
FIG. 6 is a top view of the dental comparator device of FIG. 5.

Turning now to FIGS. 5 and 6, a dental comparator device according to a second embodiment of the invention is shown. The dental comparator device 110 includes an elongate tubular body 112 having a first end 114 and a second end 116. A polychromatic light source 118 is provided within the body 112 and a lens 120 is provided at the second end 116 to transmit light from the light source 118. The lens 120 is preferably transparent, but may be colored, polarized, or otherwise constructed to provide light filtering capabilities. A parabolic reflector 121 is preferably provided behind (or proximal) the light source to focus light through the lens 120. The light source 118 is powered by a DC power source 122, which is inserted into the body 112 by removing an end cap 124 thread onto the first end 114. A power switch 126 is provided to supply and remove power from the power source 122 to the light source 118.

An articulating first boom 130 is provided having first and second arms, 132, 134, respectively. The first arm 132 includes first and second bores 136, 138 located at either end of the first arm. The second arm 134 includes a bore 140 at one end and a standard holder 142 at the other end. The first and second arms 132, 134 are coupled by placement of a coupling screw 144 (FIG. 6) through the second bore 138 of the first arm 132 and the bore 140 of the second arm 134. The coupling screw 144 may be tightened to substantially fix the first arm relative to the second arm, or loosened to permit the first and second arm to be relatively reconfigured.

An articulating second boom 150 is provided having first and second arms, 152, 154, respectively. The first arm 152 includes first and second bores 156, 158 located at either end of the first arm. The second arm 154 also includes first and second bores 160, 162 located at either end of the second arm. The first and second arms 152, 154 are coupled by placement of a coupling screw 164 through the second bore 158 of the first arm 152 and the first bore 160 of the second arm 154. The coupling screw 164 permits the first and second arms 152, 154 to be moved or fixed relative to each other, as desired.

A magnifying attachment 170 is coupled to the second arm 154 of the second boom 150. The magnifying attachment 170 includes a round magnifying lens 172 circumferentially surrounded by a casing 174. A coupling pin 176 is fixed to the casing 174 and extends through the second bore 162 of the second arm, where it is capped with a threaded nut 178. The magnifying attachment 170 is rotatable relative to the second arm 154 of the second boom 150 at the coupling pin 176.

The first and second booms 130, 150 are coupled to the body 112 with a set screw 180 having an enlarged head 182. The set screw 180 extends through the first bore 136 of the first arm 132 of the first boom 130, and the first bore 156 of the first arm 152 of the second boom 150. Washers 184, 186, 188, are preferably provided between the body 112 and the first arm 132 of the first boom 130, between the first arm 132 of the first boom 130 and the first arm 152 of the second boom 150, and between the first arm 152 of the second boom 150 and the enlarged head 182 of the set screw 180. The set screw 180 extends through each of the washers 184, 186, 188 as its extends through the bores of the first arms of the first and second booms. Preferably the washers 184, 186, 188 have a low friction surface, enabling the booms to move smoothly relative to each other when desired, but also maintain the first and second booms in relative positions when they are not actively being repositioned. The washers are preferably made of polyethylene.

In operation, the dentist provides a dental standard 180 to the standard holder 142 at the end of the articulating first boom 130. Power is provided to the light source 118 and polychromatic light is transmitted through the filtering lens 120. If not already appropriately positioned, the first boom 130 is articulated about one or both of the set screw 180 and the coupling screw 144 to position the dental standard in the path of the light. Likewise, if necessary, the second boom 150 is articulated about one or both of the set screw 180 and the coupling screw 164, and the magnifying attachment 170 is rotated at the coupling pin 176 to position the magnifying lens for the dentist to view through the magnifying lens both the dental standard and the natural tooth of the patient for comparison.

Turning now to FIGS. 7, 8, and 9, a dental comparator device according to a third embodiment of the invention is shown. The dental comparator device 210 includes an elongate tubular body 212 having a first end 214 and a second end 216. Coupled to the outside of the tubular body by a collar 222 are a first boom 218 and a second boom 220. The collar 222 frictionally engages the outside of the tubular body 212. The first boom 218 extends beyond the second end 216 of the body, bends at 224 laterally away from the axis A of the body, and terminates in a magnetic standard holder 226. The second boom 220 extends beyond the second end 216, bends laterally away from axis A at 230, and is provided with an end 232. A substantially semicircular magnifying lens support 234 is rotatably coupled by a pin 236 to the end 232 of the second boom 220. The lens support 234 is provided with two bores 240, 242 at 180° of separation. A magnifying attachment 244 includes a round magnifying lens 246 circumferentially surrounded by a casing 248. Coupling pins 250, 252 are fixed to the casing 248 at 180° of separation, and extend through the two bores 240, 242 to rotatably couple the magnifying attachment 244 to the lens support 234. It will be appreciated that the magnifying lens may thereby be rotated for viewing in any direction therethrough.

A fiber optic cable 260 adjacent a polychromatic light source 262 provided in a housing 264 separate from the tubular body 212 extends from the first end 214 of the tubular body through the body and beyond the second end 216 of the body. The light source is preferably powered by a DC power source 266.

In operation, the metal post 270 of a dental standard 272 is magnetically coupled to the magnetic standard holder 226. The dentist activates the power source to provide power to the light source 262 such that light from the light source travels through the fiber optic cable 260 to be emitted by the cable at the second end 216 of the tubular body 212. The dentist positions the magnifying attachment such that he or she may view through the magnifying lens both the dental standard 272 and at least a portion of one or more natural teeth of the patient and make a subjective judgment as to whether the color of the dental standard matches the tooth or teeth. It will be appreciated that the magnetic holder 226 provides a means for rapidly substituting dental standards through the use of a single hand.

There have been described and illustrated herein several embodiments of a dental comparator device. While particular embodiments of the invention have been described, it is not intended that the invention be limited thereto, as it is intended that the invention be as broad in scope as the art will allow and that the specification be read likewise. Thus, while a particular polychromatic light source has been disclosed, i.e., a low voltage halogen bulb, it will be appreciated that other polychromatic light sources may be used as well. Furthermore while particular types of coupling means have been disclosed for particular connections, it will be understood other connectors (e.g., screws, pins, bolts, nuts) can be interchangeably used with little modification to the invention. Also, while both articulating and non-articulating booms have been disclosed, it will be recognized that where an articulating boom has been disclosed, a non-articulating boom may be utilized, and, likewise, where a non-articulating boom has been disclosed, an articulating boom may be substituted. In addition, while rotatable booms have been disclosed with reference to the first and second embodiments, it will be appreciated that the booms may be fixed relative to the tubular body; likewise, while fixed booms have been disclosed with reference to the third embodiment, it will be appreciated that the booms of the third embodiment may be movable relative to the tubular body. Moreover, while several means for holding a dental standard have been disclosed, it will be appreciated that each of the several dental standard holders (clamp-like holders, rotatable hub holders and magnetic holders) may be used in each of the several embodiments. In addition, while a single standard is shown being held by the clamp and magnetic holders, it will be appreciated that the clamp and magnetic holder may hold two or more standards at the same time. Moreover, while the rotatable hub is described as being disc-shaped, the rotatably hub may be of another shape, e.g., hexagonal, octagonal, square, or triangular. In addition, the rotatable hub holder may be magnetized such as to require only a single disc to couple the metal posts of dental standards to the surface thereof. Furthermore, while particular locations are shown in the drawings for coupling the booms to the tubular body, other coupling locations can likewise be used. Moreover, while the standard holder is shown coupled to a boom, it will be appreciated that the standard holder may also be provided directly to, or integrally designed with, the housing. Also, while a fiber optic cable is disclosed for transmitting light in the third embodiment, it will be appreciated that the term "fiber optic cable" is used to mean one or more fiber optical fibers. In addition, while a DC power source is preferred as it provides for a portable power source (and therefore complete portability of the dental comparator device), it will be appreciated that, in the alternative, an AC power source may be additionally or alternatively utilized with each embodiment. It will therefore be appreciated by those skilled in the art that yet other modifications could be made to the provided invention without deviating from its spirit and scope as so claimed.

What is claimed is:

1. A dental comparator device for comparing a dental standard to a natural tooth, said dental comparator device comprising:
   a) a housing;
   b) a light emitting means coupled to said housing;
   c) a holding means coupled to said housing for holding the dental standard; and
   d) a magnifying means coupled to said housing for magnifying the dental standard and the natural tooth, wherein
      said means for holding a dental standard is one of a clamp, a clip, a hub, and a magnet.

2. A dental comparator device according to claim 1, further comprising:
   e) a DC power source for providing power to illuminate said light emitting means.

3. A dental comparator device according to claim 1, wherein:
   said magnifying means has a power in the range of two to twenty times power.

4. A dental comparator device according to claim 1, wherein:
   said housing has a first end and a second end and a longitudinal axis, and said magnifying means is circular in shape and has a diameter, said magnifying means being coupled to said second end of said housing such that said diameter of said magnifying means is oriented parallel to said longitudinal axis.

5. A dental comparator device according to claim 4, further comprising:
   e) a light transmitting means for transmitting light from said light emitting means towards the natural tooth, said light transmitting means being coupled to said second end of said housing opposite said magnifying means.

6. A dental comparator device according to claim 1, wherein:
   said housing includes a viewing side and a side opposite said viewing side, said means for holding the dental standard being coupled to said housing on said side opposite said viewing side.

7. A dental comparator device according to claim 1, further comprising:
   e) a first boom having first and second ends, said first end of said first boom being coupled to said housing, and said second end of said first boom being coupled to said magnifying means.

8. A dental comparator device according to claim 7, wherein:
   said first boom is articulable.

9. A dental comparator device according to claim 7, wherein:
   said magnifying means is rotatable relative to said first boom.

10. A dental comparator device according to claim 7, further comprising:
    e) a second boom having first and second ends, said first end of said second boom being coupled to said housing and said second end of said second boom being coupled to said means for holding a dental standard.

11. A dental comparator device according to claim 1, further comprising:
    e) a filter means coupled to said housing for filtering light emitted by said light emitting means.

12. A dental comparator device according to claim 1, further comprising:
    e) a collar coupling said magnifying means and said holder means to said housing.

13. A dental comparator device according to claim 1, wherein:
    said light emitting means is a polychromatic light source.

14. A dental comparator device according to claim 13, wherein:

said polychromatic light source is a halogen bulb.

15. A dental comparator device for comparing a dental standard to a natural tooth, said dental comparator device comprising:
   a) a housing;
   b) a light emitting means coupled to said housing;
   c) a holding means coupled to said housing for holding the dental standard;
   d) a magnifying means coupled to said housing for magnifying the dental standard and the natural tooth; and
   e) a first boom having first and second ends, said first end being coupled to said housing and said second end being coupled to said means for holding a dental standard.

16. A dental comparator device according to claim 15, wherein:
   said first boom is articulable.

17. A dental comparator device according to claim 15, wherein:
   an axle is provided at said second end of said first boom and said means for holding a dental standard is a hub rotatably mounted on said axle, said hub including first and second opposing members which frictionally engage the dental standard.

18. A dental comparator device according to claim 17, wherein:
   said first and second opposing members are resilient and are circular in shape.

19. A dental comparator device for comparing a dental standard to a natural tooth, said dental comparator device comprising:
   a) a housing;
   b) a light emitting means coupled to said housing;
   c) a holding means coupled to said housing for holding the dental standard; and
   d) a magnifying means coupled to said housing for magnifying the dental standard and the natural tooth, wherein
   said housing includes a distal end and said light emitting means is coupled to said housing by a fiber optic cable which extends from said light emitting means to said distal end of said housing.

* * * * *